US011517256B2

(12) United States Patent
Den Brinker et al.

(10) Patent No.: US 11,517,256 B2
(45) Date of Patent: Dec. 6, 2022

(54) METHOD OF CHARACTERIZING SLEEP DISORDERED BREATHING (71) Applicant: KONINKLIJKE PHILIPS N.V., Eindhoven (NL)

(72) Inventors: Albertus Cornelis Den Brinker, Eindhoven (NL); Okke Ouweltjes, Veldhoven (NL); Armin Gerhard Kohlrausch, Eindhoven (NL); Koray Karakaya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 393 days.

(21) Appl. No.: 16/471,811

(22) PCT Filed: Dec. 26, 2017

(86) PCT No.: PCT/EP2017/084581
§ 371 (c)(1),
(2) Date: Jun. 20, 2019

(87) PCT Pub. No.: WO2018/122217
PCT Pub. Date: Jul. 5, 2018

(65) Prior Publication Data
US 2020/0113514 A1 Apr. 16, 2020

Related U.S. Application Data (60) Provisional application No. 62/439,515, filed on Dec. 28, 2016.

(51) Int. Cl.
*A61B 7/00* (2006.01)
*A61B 5/00* (2006.01)

(52) U.S. Cl.
CPC .......... *A61B 5/4818* (2013.01); *A61B 5/7203* (2013.01); *A61B 5/725* (2013.01);
(Continued)

(58) Field of Classification Search
CPC ..... A61B 5/4818; A61B 5/7203; A61B 5/725; A61B 5/7275; A61B 5/7282; A61B 7/003
See application file for complete search history.

(56) References Cited

U.S. PATENT DOCUMENTS

| 2003/0000528 A1* | 1/2003 | Eklund | A61M 16/0051 128/204.23 |
| 2004/0102710 A1* | 5/2004 | Kim | G06K 9/00523 600/509 |

(Continued)

FOREIGN PATENT DOCUMENTS

| JP | H09212198 A | 8/1997 |
| JP | 2016002189 A | 1/2016 |

(Continued)

OTHER PUBLICATIONS

Sola-Soler, Jordi, et al. "Formant frequencies of normal breath sounds of snorers may indicate the risk of Obstructive Sleep Apnea Syndrome." 2008 30th Annual International Conference of the IEEE Engineering in Medicine and Biology Society. IEEE, 2008. (Year: 2008).*

(Continued)

*Primary Examiner* — Andrey Shostak (57) ABSTRACT

A method of characterizing a patient's disordered breathing during a sleeping period includes performing a first partial characterization of a time axis of an audio signal in order to learn the most prominent and highly relevant events. Only at a later stage, i.e., after sufficient observation of the highly relevant events, is a full segmentation of the entire time axis actually carried out. Linear prediction is used to create an excitation signal that is employed to provide better segmentation than would be possible using the original audio signal alone. Warped linear prediction or Laguerre linear prediction is employed to create an accurate spectral representation with flexibility in the details provided in different frequency ranges. A resonance probability function is generated to further characterize the signals in order to identify disor- (Continued)

dered breathing. An output includes a characterization in any of a variety of forms of identified disordered breathing.

9 Claims, 7 Drawing Sheets

(52) U.S. Cl.
 CPC .......... *A61B 5/7275* (2013.01); *A61B 5/7282* (2013.01); *A61B 7/003* (2013.01)

(56) References Cited

U.S. PATENT DOCUMENTS

| | | |
|---|---|---|
| 2004/0221848 A1 | 11/2004 | Hill |
| 2007/0118054 A1 | 5/2007 | Pinhas |
| 2007/0124136 A1 | 5/2007 | Den Brinker |
| 2007/0282212 A1 | 12/2007 | Sierra |
| 2009/0062675 A1* | 3/2009 | Weigand .............. A61B 5/0803 600/529 |
| 2009/0204397 A1 | 8/2009 | Brinker |
| 2014/0155773 A1* | 6/2014 | Stamatopoulos ...... A61B 7/003 600/529 |
| 2014/0188006 A1* | 7/2014 | Alshaer ................ A61B 5/7475 600/586 |
| 2016/0081651 A1* | 3/2016 | Nam ...................... A61B 7/003 600/529 |

FOREIGN PATENT DOCUMENTS

| | | |
|---|---|---|
| WO | 2010054481 A1 | 5/2010 |
| WO | 2013005201 A1 | 1/2013 |

OTHER PUBLICATIONS

White, Benjamin M., et al. "Investigation of a breathing surrogate prediction algorithm for prospective pulmonary gating." Medical physics 38.3 (2011): 1587-1595. (Year: 2011).*

Sola-Soler, Jordi et al., "Formant frequencies of normal breath sounds of snorers may indicate the risk of obstructive sleep apnea syndrome", 30th Annual International IEEE EMBS Conference, Aug. 2008.

International Search Report and Written Opinion, International Application No. PCT/EP2017/084581, dated Mar. 20, 2018.

H. W. Strube, "Linear prediction on a warped frequency scale," J. Acoust. Soc. Amer., vol. 68, pp. 1071-1076, 1980.

A. Härmä, M. Karjalainen, L. Savioja, V. Valimaki, U. K. Laine, and J. Huopaniemi, "Frequency-warped signal processing for audio applications," J. Audio Eng. Soc., vol. 48, pp. 1011-1031, 2000.

A.C. den Brinker, V. Voitishchuk and S.J.L. van Eijndhoven, 'IIR-Based Pure Linear Prediction.' IEEE Trans. Speech and Audio Processing 12 (1), pp. 68-75, 2004.

A. Azarbarzin and Z.M.K. Moussavi, Automatic and Unsupervised Snore Sound Extraction From Respiratory Sound Signals, IEEE Trans. Biomed. Eng., vol. 58 (5), May 2011, pp. 1156-1162.

Cohen, A. et al., "Analysis and automatic classification of breath sounds", IEEE Transactions on Biomedical Engineering, vol. BME 31, No. 9, Sep. 1984.

Karunajeewa, A. et al., "Silence-breathing-snore classification from snore-related sounds", Physiological Measurement, 2008.

Laine, U. et al., "Warped Linear Prediction (WLP) in Speech and Audio Processing", Helsinki University of Technology, Finland, 1994.

* cited by examiner

METHOD OF CHARACTERIZING SLEEP DISORDERED BREATHING

BACKGROUND OF THE INVENTION

1. Field of the Invention

The present invention pertains to a method and apparatus for monitoring breathing during a period of sleep and, in particular, pertains to a method of characterizing sleep disordered breathing (SDB).

2. Description of the Related Art

It is well understood that sleep disordered breathing (SDB) can occur as a result of some type of an obstruction in the airway of a patient, i.e., an individual who experiences SDB. Various types of obstructions can be distinguished from one another based upon an anatomical/physiological perspective, and particular types of obstructions often create particular types of sounds during the resultant SDB. A distinguishing feature of the sound that occurs during SDB is its spectral signature. For example, the sound can be a palatal snoring, which is associated with a low frequency spectrum in the range of 100-200 Hz. By way of further example, an SDB event known as stridor typically is characterized by sounds that are much higher in the frequency spectrum, perhaps several kHz. Reference is made generally to "Subject Independent Identification Of Breath Sounds Components Using Multiple Classifiers" (Alshaer, Hisham; Pandya, T. Aditya; Bradley, Douglas; and Rudzicz, Frank, 2014 IEEE Int'l Conf. on Acoustic, Speech and Signal Processing (ICASSP)).

One of the parameters that is especially relevant in SDB analysis is the amount of time during which the SDB phenomenon occurs, such as the amount of time that SDB occurs relative to the overall sleep duration, or the percentage of the respiration cycles in which SDB is observed. In order to provide accurate results, all times during the period of sleep that are somehow associated with SDB need to be identified. In the instance of snoring or wheezing occurring during SDB, the identification of longer segments of audible breathing patterns including snoring, by way of example, is different from identifying several short or individual snores. If it is necessary to characterize all periods of SDB during a period of sleep for such an analysis, it has typically been necessary to know a personalized signature of the type of event that is being sought to be identified. The problems with identifying all periods of SDB is aggravated by the fact that for even a single person the character of the SDB may change depending upon circumstances, such as through the usage of medication or the drinking of alcohol, which may have effects on the character of the sounds. Moreover, changes may occur during the course of the sleeping period, such as wherein whistling exhalation sounds occur early during a sleeping period, and heavy snoring occurs later during the sleeping period.

In the case of heavy snoring, the heavy snoring episodes typically can be readily identified based upon the intensity, energy, or loudness pattern, i.e., the strength of the signal. Consequently, the snoring episodes often can be separated from the other episodes (i.e., the non-snoring episodes). A common characterization of the snoring episodes can be made by any convenient frequency transformation methodology, i.e., Fourier Transformation (FT), power spectral density function (PSD), or the transfer function of the synthesis filter of an estimated linear prediction system. The latter approach is, however, limited due to the fact that the dominant spectral energy in SDB sounds may range from very low (100 Hz) to fairly high (several kHz), and especially the low-frequency modeling capabilities of conventional linear prediction methodologies are typically poor.

In certain cases, the energy or loudness of the SDB events is not always a sufficient trigger to identify any given SDB episode as being one of interest. Other events may trigger loud sounds, such as speech, sneezing, and the like, that are not associated with the types of audible characteristics that are searched for as being characteristic SDB sound features. Therefore, it is necessary to provide methods for identifying SDB events that are more advanced and robust.

Another commonly employed aspect to improve the identification of SDB events is an analysis of the periodicity of the envelope or energy of the signal. However, this does not always provide the desired results. This is especially the case in a natural environment such as a domestic bedroom where preferably the sound is analyzed by an unobtrusive sound monitor (such as a microphone situated within the bedroom), wherein certain background noises may dominate such that even when certain repetitive audio occurrences are spectrally clearly audible and observable (such as in a spectrogram), a system for separating episodes based upon overall quasi-periodic loudness variations may not work.

A possible way that has been attempted to overcome these shortcomings is to consider multiband analysis. For specific bands, the quasi-periodicity will be visible. However, a clear drawback to such an approach is the need for the design of filters as well as a complicated decision logic. Improvements thus would be desirable.

SUMMARY OF THE INVENTION

Accordingly, it is an object of the present invention to provide a method of characterizing sleep disordered breathing that overcomes the shortcomings of conventional methods. This object is achieved according to one embodiment of the present invention by providing a method that includes receiving at least a first signal that is representative of the sounds occurring during at least a portion of the sleeping period in the vicinity of the patient, identifying in the at least first signal a plurality of segments, characterizing at least some of the segments of the plurality of segments as each being in one of a plurality of pre-established clusters, the plurality of pre-established clusters each having a plurality of properties, a property from among the plurality of properties being a phase from among a group of phases that comprises an inhalation phase of a breathing cycle, an exhalation phase of a breathing cycle, a rest phase of a breathing cycle, and an unknown event, another property from among the plurality of properties being an energy level from among a group of energy levels that comprises a high energy level and at least one of a low energy level and a medium energy level, applying to each segment of the at least some of the segments a spectral characterization of the segment, for at least one segment characterized as being in a cluster having as its phase an unknown event, re-characterizing the at least one segment into being characterized as in another cluster having as its phase one of an inhalation phase of a breathing cycle, an exhalation phase of a breathing cycle, and a rest phase of a breathing cycle based at least in part upon a correspondence between the spectral characterization of the at least one segment and a spectral characterization that pertains to the another cluster to form a time axis that corresponds with the at least first signal and whose segments are each categorized as being one of an inhalation phase of a breathing cycle, an exhalation phase of a breathing cycle, and a rest phase of a breathing cycle, and generating an output that comprises information that is based at least in part upon the time axis.

It is yet another object of the present invention to provide another method of characterizing sleep disordered breathing that overcomes the shortcomings of conventional methods. This object is achieved by providing a method that includes receiving at least a first signal that is representative of the sounds occurring during at least a portion of the sleeping period in the vicinity of the patient, identifying in the at least first signal a plurality of segments by: subjecting at least a portion of the at least first signal to a linear prediction algorithm to obtain an excitation signal that is representative of the at least portion of the at least first signal, identifying as a plurality of candidate transition points in the excitation signal a plurality of simultaneous occurrences of a low energy level and a rapid change in the excitation signal between a negative slope and a positive slope, such as by using short-term polynomial decomposition, by way of example, determining that a plurality of portions of the excitation signal that exist between pairs of candidate transition points are similar to one another based at least in part upon similarity of the period and the spectral content of the plurality of portions, based upon an application of an auto-correlation function, by way of example, and based at least in part upon the determining, concluding that: the pairs of candidate transition points are actual transition points, a portion of the excitation signal that immediately precedes each actual transition point is an inhalation phase of a breathing cycle, and a portion of the excitation signal that immediately follows each actual transition point is an exhalation phase of a breathing cycle, and generating an output that comprises information that is based at least in part upon at least one of the inhalation phases and the exhalation phases.

It is yet another object of the present invention to provide another method of characterizing sleep disordered breathing that overcomes the shortcomings of conventional methods. This object is achieved by providing a method that includes receiving at least a first signal that is representative of the sounds occurring during at least a portion of the sleeping period in the vicinity of the patient, subjecting at least a portion of the at least first signal to a linear prediction algorithm to obtain a transfer function that is equal to a numerator polynomial divided by a denominator polynomial, determining one or more roots of the numerator polynomial, at least some of the roots of the one or more roots each being in the form of a complex number that can be represented by a vector having a length and further having an angle with respect to an abscissa, generating for each root of the at least some of the roots a probability component that follows a template probability having a given shape and having a height and a width by: determining a center frequency of the probability component based at least in part upon the angle of the root's vector, and determining a width of the probability component based at least in part upon the length of the root's vector, and forming a probability function by combining together the probability components. The linear prediction algorithm may employ a warping factor, and the warping may be selectable and changeable to steer to analysis to a particular region of interest.

An aspect of the invention is to provide a methodology for sound analysis in order to create indicators of the type and severity of the SDB with a minimum of need of a priori or personalized data. Especially, an aspect of the invention is to outline a robust system for differentiated SDB event characterization, including duration indicators. A typical way of addressing this issue is by a chain of processing beginning with segmentation, followed by spectral characterization and identification. In contrast to these attempts, the invention has improved some parts and added flexibility. With respect to the added flexibility, in a cascaded approach, previous incorrect decisions were made at early stages (i.e., segmentation) which has hampered further processing or reduced the quality of the second steps. The flexibility envisioned in the invention mitigates this shortcoming.

In particular, the invention envisions performing a first partial characterization of a time axis in order to learn the most prominent and highly relevant events. Only at a later stage, i.e., after sufficient observation of the highly relevant events, is a full segmentation of the entire time axis actually carried out.

Another aspect of the invention is to provide a method of performing sound analysis which can easily separate SDB-specific episodes from other episodes without resorting to multiband analysis.

Another aspect of the invention is to present a methodology for generating inhale/exhale transitions and to identify inhale/exhale time stretches.

A further aspect of the invention is to provide a sound analysis methodology which can easily separate SDB-specific episodes from other episodes without resorting to multiband analysis, and which can handle this for extremely low-frequency snoring phenomena (such as at 100 Hz, by way of example) as well as for high frequency snoring phenomena such as whistling or stridor phenomena which occur at several kHz.

Another aspect of the invention is to present the results of the analysis in a convenient and easily understandable format.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As noted above, an aspect of the solution presented by the invention is to employ a four-stage analysis approach in order to identify all SDB events during a period of sleep of a patient. Another aspect of the invention is to use the best analysis tools that can be employed as well as to employ soft decisions or hard decisions only for cases for high probability.

The method typically begins with receiving a signal that is representative of the sounds that occur during a sleeping period in the vicinity of a patient. In some instances, the reception of the signal occurs through the use of a microphone that may or may not be a part of a device such as a cellular telephone or other such device employed by the patient. Certain of the processing of the signal that is described in greater detail below can be performed on such a cellular telephone or other such device that incorporates a computer and that is employed by the patient. In other circumstances, greater degrees of processing and further analysis may be performed remotely from the patient by technicians or other expert individuals at a location remote from the patient using other computer equipment.

As will be set forth in greater detail below, the first stage can be described as performing temporal segmenting of the signal into segments when such segments are easily recognizable, i.e., with a high degree of probability, as being instances of SDB or other specific events. The segments, as will be set forth in greater detail below, are usable to identify breathing cycles. In the second stage, the segments are further characterized and are each clustered or categorized into one of a plurality clusters, wherein the clusters (or at least the definitions thereof) may be pre-established. In the third stage, the spectral signatures of the clusters are used for a further, i.e., complete, automated annotation of the entire signal that is representative of all of the sounds occurring during the sleeping period. In the fourth stage, the clusters and, more particularly, their duration, are evaluated in order to determine the relative time over the course of the sleeping period during which the events of any given cluster have occurred. For instance, the output may be (by way of example) a summary of the sleeping period comprising the total periods of snoring, the total periods of non-SDB sleep, etc., and this data may be output in any of a variety of fashions. The output possibly may be augmented with other characterizations of the events of any one or more of the clustered occurrences.

More specifically regarding the first stage, an audio signal is picked up by a microphone, such as of a cellular telephone or other device. The audio signal can be recorded for later processing, either on a cellular telephone or elsewhere, or the signal can be processed contemporaneously with its being recorded. Preferably, an analysis of the signal is performed by creating an excitation signal using a linear prediction algorithm. From the excitation signal, the energy is determined. It is also possible to include spectral features at this point, such as Mel Frequency Cepstral Coefficients (MFCC) or the like. An autocorrelation function (ACF) can be used to determine if there is sufficient periodicity in the expected range, i.e., such as by setting thresholds on the range in which the repetition rate is desired and setting a minimum value for the strength or degree of correlation from the ACF. The ACF can be any of a wide variety of known ACF systems that are generally available and are notoriously well known in the relevant art. Such an ACF desirably will be made to operate over several periods of breathing during the sleeping period, and still preferably it is configured to identify only those segments, which are, on average, sufficiently repetitive according to the range and strength settings, by way of example. That is, the ACF is not configured to identify individual breathing cycles.

With regard to the repetition rate, the energy signal or a suitably created envelope signal will be characterized by two clearly distinguishable levels. These can be estimated by clustering algorithms, of which many are known to exist. A threshold can be set to ensure sufficient separation.

By these two measures, segments can be identified that are clearly indicative of SDB events and, more particularly, of SDB sounds that occur during SDB events. The various thresholds can be set such that the segments that are identified as including SDB events are of a very high reliability, i.e., a high specificity.

A subdivision of the time axis can be made in terms of breathing cycles based upon the estimated repetition rate. Each breathing cycle can be divided into parts belonging to one of a plurality of pre-established clusters or a probability of belonging to a certain cluster or level. Most typically the parts will sequentially be an inhalation phase, and exhalation phase, and a rest phase immediately before the next inhalation. It may be possible to employ a time marker to indicate transitions from inhalation to exhalation. A number of examples of this will be set forth below.

The clusters can have properties, and in the depicted exemplary embodiment the clusters are each given as their properties an energy level and a phase. For instance, the energy levels are either high energy or low energy. It is understood that other energy levels or additional energy levels can be employed. Furthermore, it is expressly noted that a signal envelope level can be used in place of an energy level at any points herein where an energy level is mentioned. As is generally understood, an amplitude can refer to some measure of energy over a period of time, such as over a segment of a breathing cycle, and it can refer to the energy of the (excitation) signal. Another option is to look at the envelope of the signal, which refers to the mean of the excitation signal, which is equally relevant. Another of the properties is a phase of the breathing cycle which, in the depicted exemplary embodiment, includes an inhale phase, an exhale phase, a rest phase, and an unknown phase, i.e., one in which it is uncertain whether the phase is inhale or exhale or rest. The exemplary clusters numbered 1 through 6 are characterized as being of high probability. An additional cluster 7 is for medium and low probability examples that otherwise would have been in one of clusters 1-6.

Each time instance or period is thus characterized as belonging to a cluster from among a plurality of pre-established clusters, such as are identified in the following Table 1, which presents a case involving clusters defined as each being of one of two energy levels (high and low).

TABLE 1

| Cluster | Level | Phase | Probability |
| --- | --- | --- | --- |
| 1 | High | Inhale | High |
| 2 | High | Exhale | High |
| 3 | High | Unknown | High |
| 4 | Low | Inhale | High |
| 5 | Low | Exhale | High |
| 6 | Low | Unknown | High |
| 7 | | | Medium or low for clusters 1-6 |

More specifically, an aspect of the invention is to use an excitation signal that results from the application of some type of linear prediction, preferably one that employs a line of tapped allpass filters such as Warped Linear Prediction (WLP) or Laguerre Linear Prediction (LLP) to an original input (audio) signal. As is understood in the relevant art, both WLP and LLP use a line of tapped allpass filters, but in LLP the first filter is different from that of WLP. Several advantages exist in using the energy or envelope of the excitation signal instead of or in combination with that of the original audio signal for signal segmentation and segment identification. These advantages are set forth below.

First, the background noise (silence or fixed noised such as ventilation fans, and the like) level is more steady in the energy of the excitation signal than in the energy of the original audio signal, thus making the excitation signal a more reliable source for signal segmentation. Second, the differentiation between the aforementioned background (i.e., silence) level and an SDB event is typically more pronounced in the excitation signal than in the original audio signal. This is especially the case if the SDB sound has a more high frequency character. Third, the excitation signal shows more clearly the transition from inhalation to exhalation.

A general linear predictor is given by:

$$H(z)=1-\Sigma b_k G_k(z)$$

with $G_k(z)$ being an arbitrary transfer function, with $b_k$ being weights with $\Sigma$ being the summation sign and the summation ranging over all ks (k=1, 2, . . . . K, with K being the number of degrees of freedom in the system). H(z) is referred to as the analysis filter.

In a conventional linear prediction algorithm, $$G_k(z)=z^{-k}$$

being known as a tapped-delay-line filter, and for warped linear prediction, $$G_k(z)=A^k(z)$$

where A(z) is a first order allpass section defined by a real warping factor or pole (p) with −1<p<1. As is generally understood in the relevant art, a first-order allpass filter A(z) having pole p is given by:

$$A(z)=(p-z^{-1})/(1-pz^{-1})$$

The analysis filter H(z) is optimized in such a way that when filtering the original input signal x(t) by this system, the output signal has minimal energy and is spectrally as flat as possible. The degrees of freedom in this optimization are the coefficients $b_k$.

The input signal x(t), which is a discrete-time segment of audio, is input into a filter system wherein k=1, 2, . . . . K, and produces outputs $y_k(t)$, meaning that $y_k(t)$ is the response of the filter $G_k(z)$ having input x(t).

A covariance matrix Q is constructed as:

$$Q_{k,l}=\Sigma y_k(t)y_l(t)$$

where the summation is over the time t.

A covariance vector is constructed as:

$$R_k=\Sigma x(t)y_k(t)$$

where the summation is over the time t.

Alternatively, the covariances may be weighted using some temporal weighting function.

The optimal parameter set is defined:

$$Q B=R$$

where the vector B includes the parameters $b_k$, i.e., B=[$b_1$, $b_2$, . . . $b_K$].

Having optimized the parameters in this way, the inverse of the amplitude of the transfer function of the analysis filter reflects the spectral properties of the original input signal x(t). The residual or excitation signal e(t) is the output of the analysis filter H(z) acting upon x(t) and is given by:

$$e(t)=x(t)-b_k y_k(t).$$

A running analysis can be made by regularly determining the optimum coefficients b and updating the coefficients b in the filter, thus creating a time-variant adaptive filter.

As such, from the input signal x(t), i.e., the full signal rather than a segment thereof, an associated excitation signal e(t) which likewise is a full signal rather than a segmented excitation signal, can be created. Alternatively, overlap-add methods can be used to construct the full excitation signal from segments e(t).

In order to detect SDB events, those time segments wherein the SDB dominantly determines the sound need to be separated from the remaining time segments wherein the sound is dominated by the background noises, which may predominantly be silence. It is easier and more robust to do such identification and segmentation based upon the excitation signal e(t) rather than based upon the original signal x(t).

As suggested above, two primary methodologies for detecting episodes with SDB sounds are 1) to identify quasi-periodic patterns of the signal energy, and 2) to identify two distinct energy levels where the loudest level corresponds to an SDB event and the lowest possible sound corresponds to background sounds. It is understood that alternative methods, i.e., methods that would not be based upon quasi-periodic patterning of the signal energy or would not be based upon the identification of two distinct energy levels, can be used for the identification of snoring or other SDB events from the original audio signal without departing from the spirit of the present invention.

Figure 1:
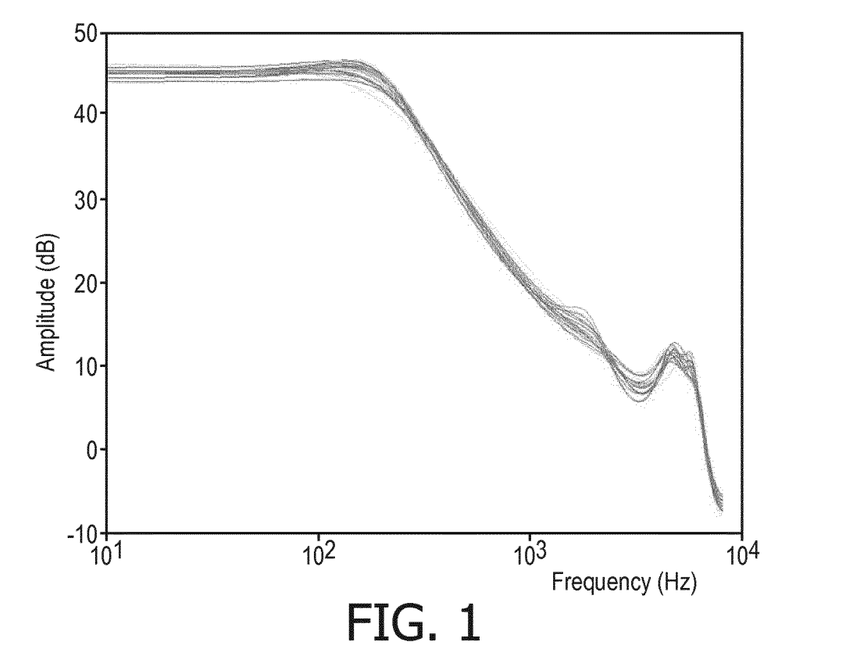
FIG. 1 is the inverse of the amplitude transfer of estimated transfer functions for a plurality of snoring episodes using a conventional linear prediction algorithm.
Figure 2:
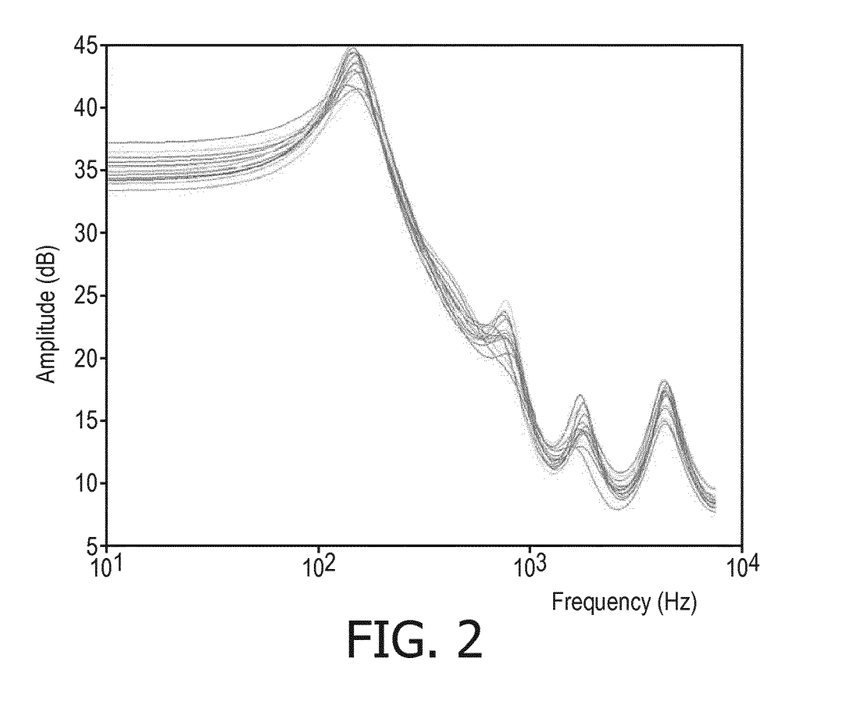
FIG. 2 is a view similar to FIG. 1 in that it provides the inverse amplitude of estimated transfer functions of the same snoring episodes, except that FIG. 2 has the inverse amplitude transfers estimated using Warped Linear Prediction (WLP)

Not only is the identification and segmentation of SDB events easier when using the excitation signal e(t) than when using the original signal x(t), it is even more desirable if the excitation signal e(t) is obtained through the use of a linear prediction algorithm other than a conventional linear prediction algorithm. As is understood in the relevant art, conventional linear prediction methodologies employ a tapped delay line. FIG. 1 depicts the inverse of amplitude transfer of transfer function H(z) of the analysis filter for a number of snoring episodes employing such conventional linear prediction. In contrast, FIG. 2 depicts a transfer function for the same snoring episodes, except employing WLP having a pole, i.e., a warping factor, of p=0.6, although it alternatively could be −0.6. As noted above, WLP employs a series of tapped allpass filters. In both cases presented in FIGS. 1 and 2, the order is K=10. As can be clearly understood from FIG. 2, the transfer function that employs WLP has a clear resonance peak at about 150 Hz, whereas this is hardly visible in FIG. 1 which employs conventional linear prediction. It is noted that the peak at 150 Hz reflects an actual dominant snoring sound frequency in the snoring events that are depicted in FIGS. 1 and 2. It thus can be understood that WLP (or LLP, by way of example) are more advantageous in creating an excitation signal e(t) than conventional linear prediction. Other advantages of using WLP or LLP, by way of example, rather than employing conventional linear prediction will be set forth in greater detail below.

Figure 3:
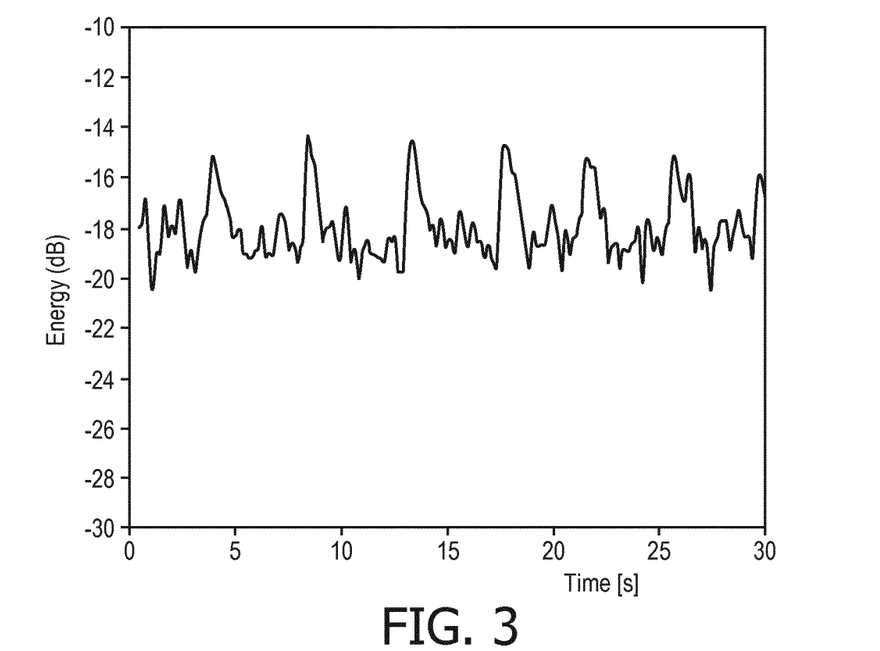
FIG. 3 depicts the running energy of an input signal.
Figure 4:
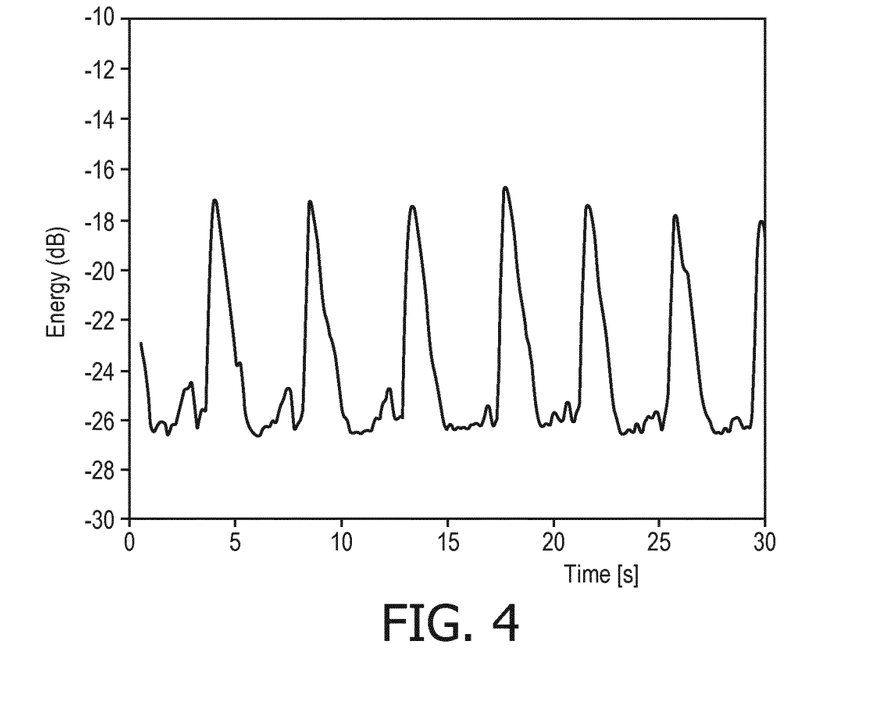
FIG. 4 depicts the running energy of an excitation signal that is obtained by subjecting the input signal of FIG. 3 to WLP.

The advantageous use of an excitation signal e(t) rather than an original audio signal x(t) is further advantageously depicted in FIGS. 3 and 4. For instance, FIG. 3 depicts the running energy of an input signal x(t). In FIG. 4, the running energy of an excitation signal e(t) that was derived from the original signal x(t) and employing WLP having a warping factor of p=0.6 for an order of K=10 is depicted. In the case of FIGS. 3 and 4, the input sound is a puffing sound during exhalation. The repeated puffing sounds are more clearly visible in FIG. 4, specifically in its excitation signal e(t), than in FIG. 3 which depicts the original signal x(t). As such, the analysis that employs WLP helps to identify other types of breathing phenomena in addition to deep snoring.

Figure 5:
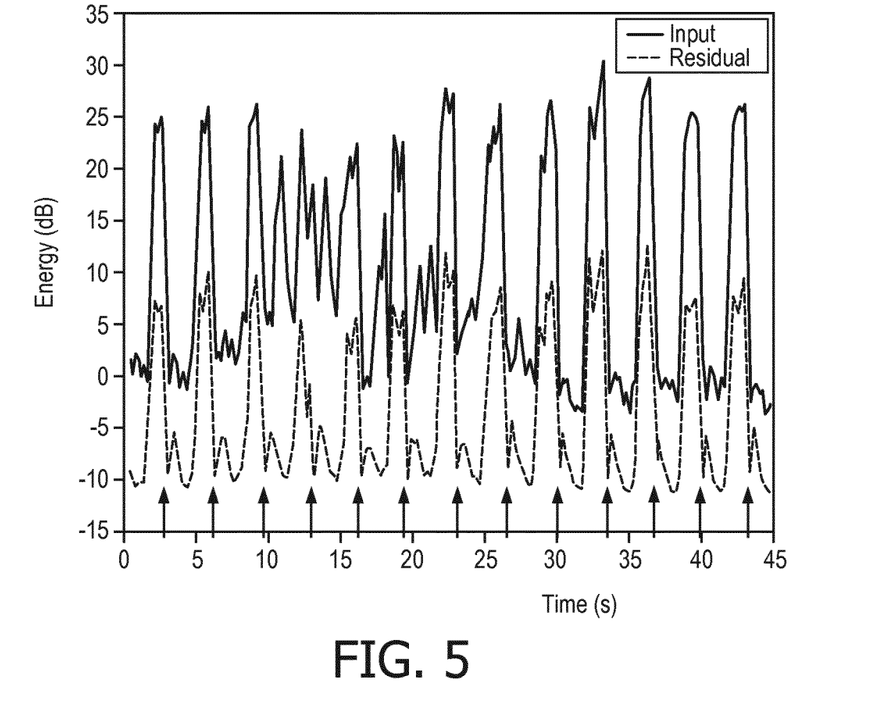
FIG. 5 is a depiction of the running energy of another input signal overlaid with another corresponding excitation signal derived therefrom and that additionally includes arrows indicating a plurality of inhale/exhale transition points.

FIG. 5 depicts a different input signal and a resultant excitation signal overlaid on one another. In the original input signal, the identification of the background is difficult between approximately 10 seconds and 30 seconds. However, this period between 10 and 30 seconds is much more regular and clearly identifiable in the excitation (i.e., residual) signal, particularly in its temporal behavior. This means that the aforementioned mechanisms, i.e., detection of quasi-periodicity and detection of distinct energy levels, will provide better results when operating on an excitation signal rather than operating upon an original signal.

Further in FIG. 5, a series of arrows are provided which indicate the transition points between an inhale and an exhale. That is, the period immediately before (i.e., to the left of) a transition point corresponds with an inhale phase of a breathing cycle, and the period immediately after (i.e., to the right of) a transition point corresponds with an exhale phase of a breathing cycle. It is noted that the inhalation and exhalation transition points are much more visible in the energy of the excitation (i.e., residual) signal than in the original (i.e., input) signal, which demonstrates that the identification of such transition points is easier in the excitation signal than in the original signal.

Figure 6:
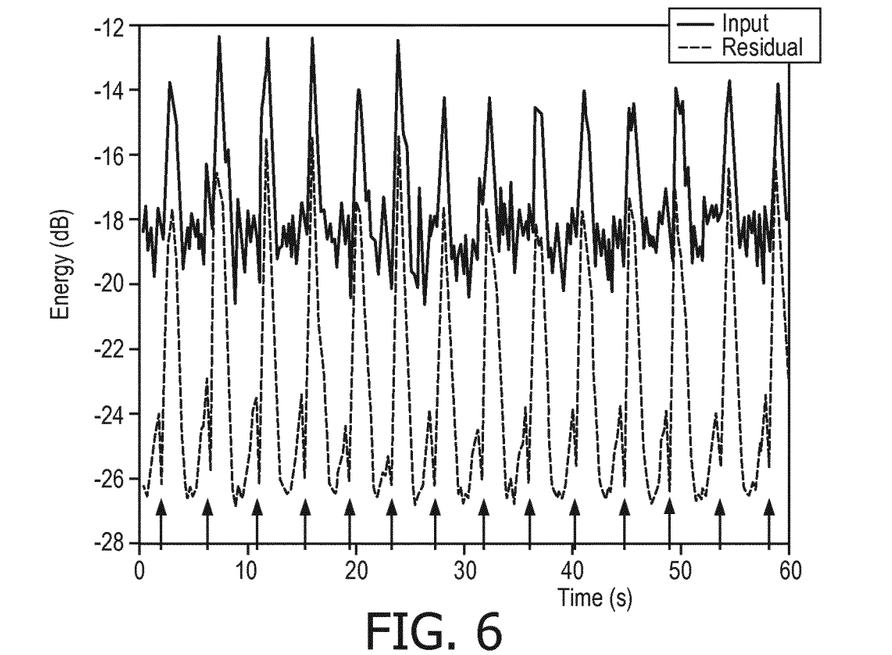
FIG. 6 is the running energy of still another input signal and still another corresponding excitation signal derived therefrom that depict with a number of arrows still other inhale/exhale transitions.

FIG. 6 depicts another exemplary input signal and resultant excitation signal (i.e., residual signal) that are overlaid with one another. Again, the excitation signal in FIG. 6 is better structured than the original input signal, and it can be seen that the low levels of energy in the original signal appear far more noisy than in the excitation signal. Again, a plurality of inhale/exhale transition points are indicted in FIG. 6 with a plurality of arrows.

The transition points identified by arrows in FIGS. 5 and 6 can be detected in the following way. The transitions between inhalation and exhalation are characterized by a simultaneous occurrence of i) high positive curvature, meaning going rapidly from a negative slope to a positive slope, and ii) low level, meaning that the energy level is at or close to the background level, although sometimes it may be at a middle level, but is essentially never at the higher levels.

Employing a short-term polynomial decomposition is a way in which the simultaneous occurrences of high curvature and low level can be identified in order to create a list of candidate transition points. In that case the running energy of the excitation signal, preferably in dB like depicted in FIG. 6 cut into overlapping segments. A polynomial function is fitted to it, preferably this fit is a least-squares fit under a weighting function. The polynomial coefficients of the fitted curve are inspected and so is the error signal. If the error is sufficiently small, the curvature is sufficiently high, and the level is sufficiently low, the segment contains the transition. The position of the transition inside the segment can be determined from the estimated polynomial coefficients. All values required in the decisions (sufficiently small, high and low) can be set dynamically e.g. by monitoring the environment or keeping track of past segments, by upfront settings (e.g., an error less than 10% of the total error, a contribution of the quadratic term in the reducing the modelling error of at least a certain percentage), or a combination of both methods. Alternatively, a classifier (e.g. a neural network) can be trained to recognize the transitions in the energy graphs. The list of candidate transition points typically includes a number of extra elements that are induced by noise and may further include some missing elements.

Following the identification of candidate transition points, an effective subsequent step is a validation operation. One can expect that the distances (i.e., the durations of time) between the transition points are regular—once or multiple times the repetition rate induced by the breathing. The repetition rate can be determined from the aforementioned autocorrelation function (ACF) or an additional or alternative ACF applied to the excitation signal, it being reiterated that numerous ACFs are notoriously well known in the relevant are and are not restated herein for reasons of brevity.

Figure 7:
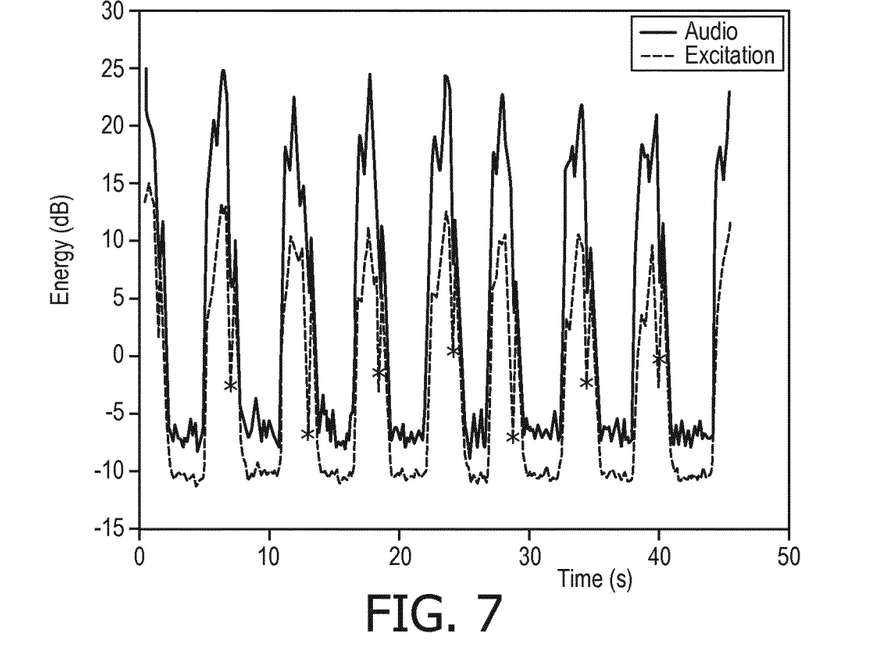
FIG. 7 depicts the running energy of a further input signal and a further corresponding excitation signal obtained therefrom overlaid with one another and depicting with asterisk symbols further inhale/exhale transitions.

Such a methodology advantageously enables the generation of candidate transition points and the validation of candidate transition points into actual transition points between an inhalation phase and an exhalation phase of a breathing cycle. Results of such processing are shown in a further example in FIG. 7, which depicts still another input (audio) signal and an excitation signal derived therefrom, with both signals being overlaid. FIG. 7 highlights two observations. First, the transition points need not always be at low levels but can also occur at middle levels, as mentioned above. In this regard, the transition points between the inhalation phase and the exhalation phase of the various breathing cycles are indicated in FIG. 7 with asterisk symbols. Second, FIG. 7 demonstrates that the mechanism described above is effective in finding the correct positions of the transition points even though a number of other instances of high curvature can be found in the excitation signal. It is noted that the energy profile of the original input (audio) signal shows clear high curvature instances which are determined to not be the desired transition points. As such, this again indicates that the excitation signal e(t) offers a better avenue for analyzing and interpreting the temporal structure of a series of SDB events than the energy profile of the original (audio) signal x(t) itself.

Having identified a plurality of transition points in a signal, the entire time signal can be divided into inhalation phases directly before the transition points, exhalation phases directly after the transition points, and rest or silence phases that are situated immediately after an exhalation phase but prior to the sequentially next inhalation phase. Such analysis is performed by advanced methodologies or straightforward heuristic methodologies (such as mentioned above). The high level SDB events can therefore also be characterized as belonging to inhalation or exhalation phases, which is of further benefit for the interpretation of the characteristics associated with particular SDB episodes.

One result of such an SDB monitoring system could employ the output of the aforementioned analysis to provide the various information. For instance, an overview of a typical spectrum during an inhalation phase, whether or not marked as being an SDB event, could be provided. Likewise, an overview of a typical spectrum during exhalation, whether or not marked as being an SDB event, could likewise be output. Also, an overview of the typical background noise spectrum could likewise be output. As is understood in the relevant art, the spectrum that is obtained during an SDB event, whether during an inhalation phase or an exhalation phase, can be helpful in diagnosing the specific cause or causes of the SDB events, which is highly desirable.

It thus can be seen that the output of stage one potentially can be a timeline, with the entire timeline being segmented between transition points of high probability. In other embodiments, however, the output of the first stage may simply be the outputting of a table such as the aforementioned Table 1.

In the second stage, the clusters and, more particularly, the segments therein, are further augmented by parameters that further describe the events. More specifically, the clusters, such as the exemplary clusters 1-7 of Table 1, are augmented by adding to each sample in each cluster a spectral characterization of the sample. Such a spectral characterization may be a Fourier Transform, a power spectral density function, or may include features that describe the spectrum such as Mel Frequency Cepstral Coefficients (MFCC), or the parameters of a linear prediction system. A linear prediction system is particularly effective inasmuch as the aforementioned parameters $b_k$ are already available from stage one in situations in which the subdivision of the signal is based upon an excitation signal wherein WLP or LLP was employed. Based on the additional spectral characterization, the clusters are checked for consistency in terms of their spectral characterization and, if necessary, are further subdivided. As a result, a set of clusters is created based at least in part upon a consistent spectral characterization. This is in addition to the clusters being based at least in part upon a consistent energy level and a consistent phase as demonstrated in the example in Table 1.

Certain aspects of this part of the invention involve the use of linear prediction methodologies that are based upon allpass filters, such as the aforementioned WLP and LLP. It is appreciated that although the use of such alternative linear prediction methodologies may result in the loss of a correspondence with a tube model of an error system, the advantage of employing WLP or LLP for SDB is a greater advantage than the loss of such a correspondence with a tube model.

In particular, the use of such WLP and LLP brings an increased spectral resolution in the low frequency range for positive settings of the warping parameter. This enables an improved spectral characterization of low frequency snoring phenomena. Additionally, a better temporal characterization results from the analysis of the excitation signal e(t), i.e., the residual or excitation signal energy, compared with the use of the original signal x(t) for high frequency phenomena such as occurs in stridor, wheezing, and puffing. Furthermore, a methodology to arrive at an interpretable spectral format is achieved by transforming the parameters from the estimated system (WLP or LLP) from various SDB episodes into a resonance probability function.

In the instant exemplary embodiment, WLP is employed, although it is understood that LLP can be employed without departing from the spirit of the instant invention. For audio coding, the exemplary warping factor or pole that is chosen is coupled to the sampling frequency of the audio signal in order to mimic the human hearing system. For example, in an instance in which the sampling rate is 30 kHz, a warping factor of p=0.7 might be employed whereas in a sampling system at 10 kHz the preferred warping factor might be p=0.6 in order to get a good correspondence with the sensitivity of the human ear over these respective ranges.

For SDB analysis it is preferred to employ the freedom of warping to deliver improved features for SDB characterization. As such, the choice of the pole or warping factor for best SDB analysis is set on different considerations. For example, the pole can be set on a priori information or, alternatively, could be optimized based upon signal characteristics using different criteria. By way of example, the use of a priori information might involve the selection of a warping factor or pole of p=−0.5 if it is desired to look more closely at high frequency phenomena, or the warping factor or pole might be chosen as p=0.5 if examination of lower frequency phenomena is desired. If different criteria are employed, the warping factor could be selected, for example, in order to minimize a mean-squared error or could be selected at a different value if mean-absolute error is desired to be minimized Still alternatively, the analysis can be steered depending upon the desired SDB analysis result, such as when it is desired to perform analysis of resonance peaks. For instance, it may be determined that a resonance peak is identified at a particular frequency, such as in the way a resonance peak at approximately 150 Hz is identified in FIG. 2. Based upon the existence peak at 150 Hz, it may be desirable to adjust the warping factor to focus on phenomena around 150 Hz. Other examples will be apparent.

As suggested above, the estimated parameters contained in the vector B define the analysis filter function H(z). The roots of its numerator polynomial can be used to determine the resonance peaks. That is, the filter function H(z) can be characterized as a numerator polynomial divided by a denominator polynomial. The roots of the numerator polynomial can be identified in any of a wide variety of fashions. In situations where one or two roots are needed to be identified, basic algebraic operations potentially may be employed to determine the roots. In situations where a greater number of roots exist, any of a wide variety of more complex root-finding algorithms, of which many are known in the relevant art, can be employed. For instance, other root finding algorithms that may be employed would include those based upon Bairstow's method or other methods such as Halley's method, Laguerre's method, Bernoulli's method, and the like without limitation.

Having various SDB episodes in a signal and having the filter parameters from the vector B, i.e., $b_k = b_1, b_2, \ldots b_K$ enables useful analysis. For each of the aforementioned SDB episodes, a resonance probability function can be determined to characterize the SDB episodes. This can be done by considering the roots of the numerator polynomial of H(z) as mentioned above. Certain of the roots of the numerator polynomial will be complex numbers characterized (a+bi) where a and b are real numbers, and where i is the imaginary unit.

It is further understood that such complex numbers can each be characterized as a vector having its own origin situated at the origin of an a-b coordinate system wherein the abscissa is the a-axis and the ordinate is b-axis. The terminus of the vector is at the point a, b on the a-b coordinate system.

The various roots of the numerator polynomial of H(z) can include one or more complex number roots and/or one or more real number roots. The real number roots are ignored, as are complex number roots lacking a positive imaginary part or lacking sufficient absolute value. In this regard, the absolute value is the length of the vector and is given by SQRT $(a^2+b^2)$. In situations where the length is 0.4 or greater, such roots (if they have a positive imaginary part) are considered to be representative of resonant phenomena. Slightly different criteria for selecting complex roots representing resonant phenomena may be used as well, e.g. where both angle and radius play a role in the selection.

Figure 8:
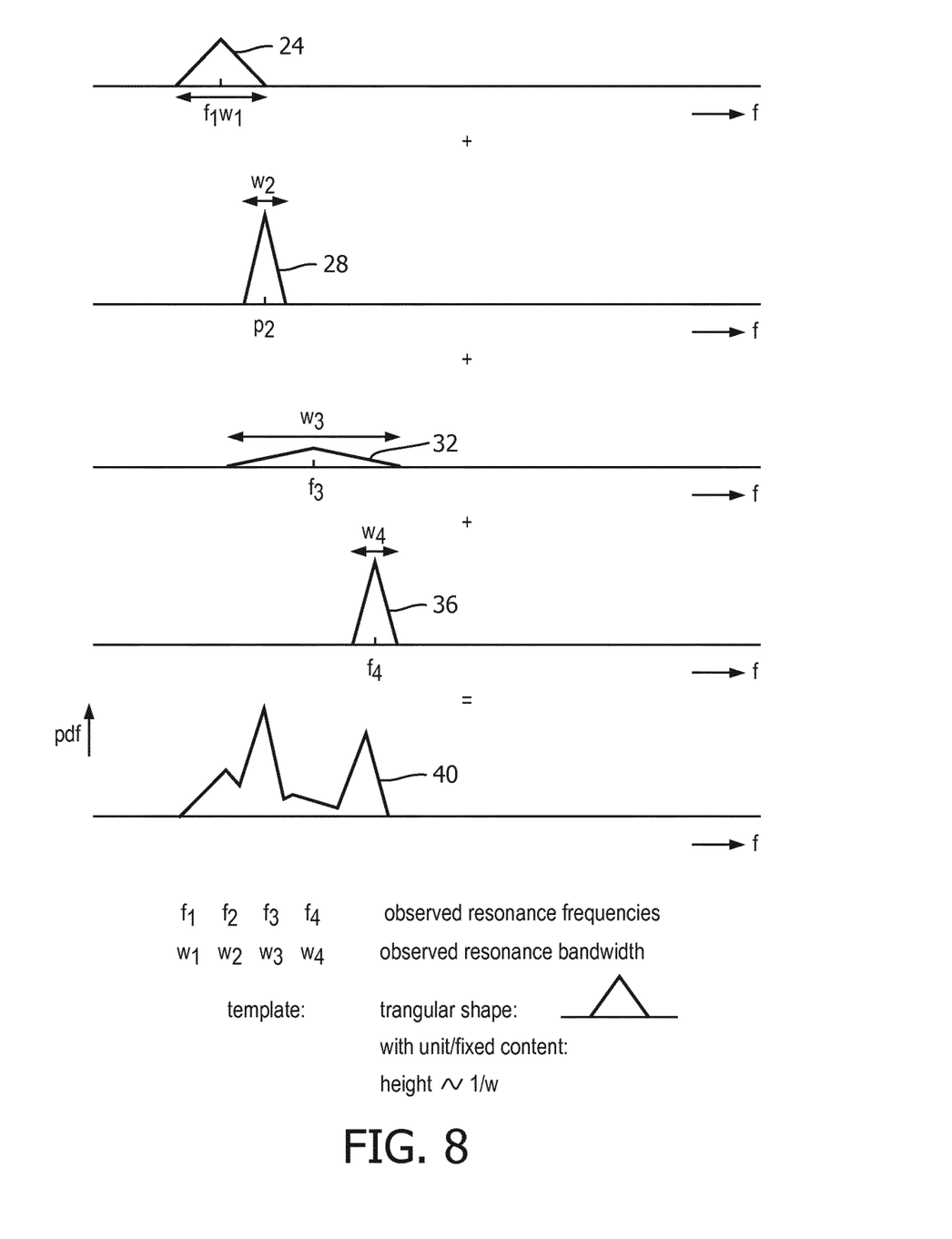
FIG. 8 is a diagrammatic explanation of the use of template probabilities each having a shape (triangular by way of example) wherein a plurality of probability components are combined into a probability function.
Figure 9:
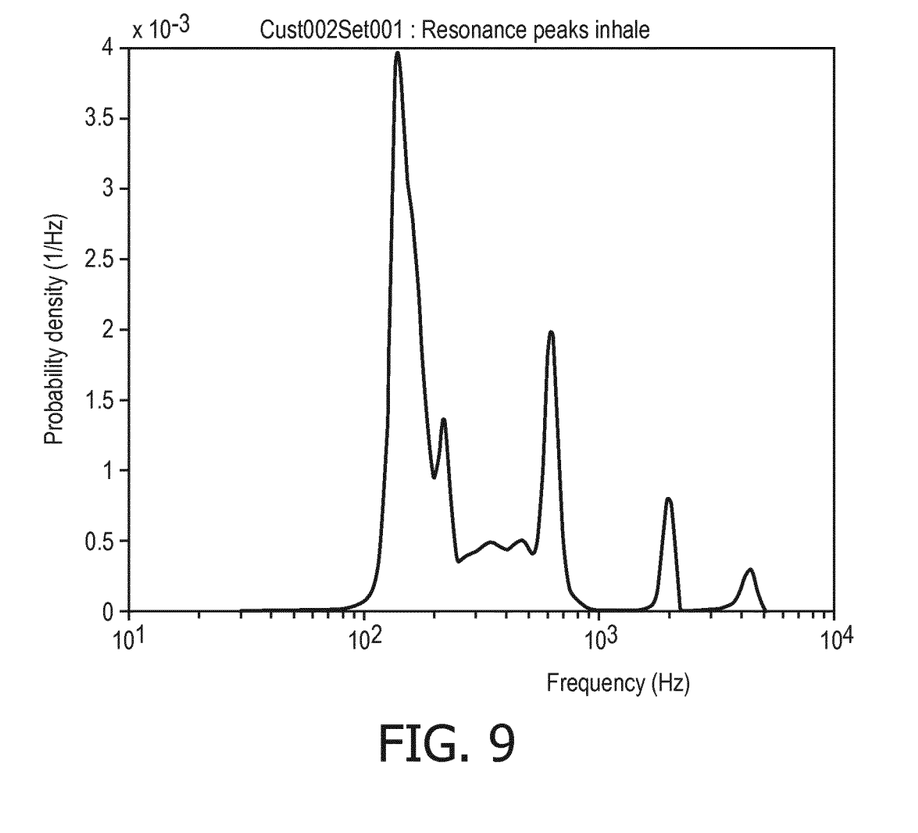
FIG. 9 is a depiction of a probability function.
Figure 10:
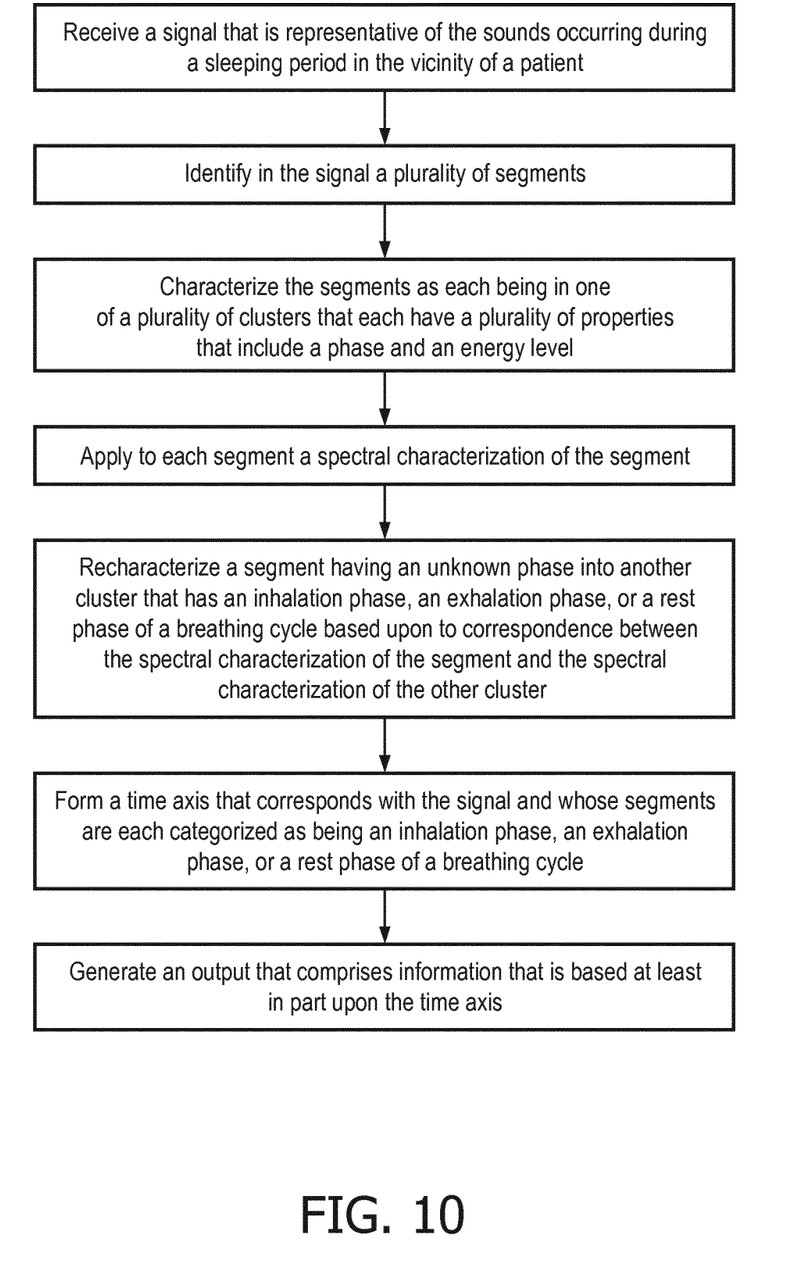
FIG. 10 is a flowchart depicting certain aspects of an improved method in accordance with the invention.

Of such complex number roots of the numerator polynomial, the angle of the vector with respect to the abscissa corresponds with a center frequency $f_i$, and the radius of the root (i.e., the length) is associated with a bandwidth $w_i$. One can then employ a template probability having a predetermined shape and can use the aforementioned angle (i.e., the center frequency $f_i$) and the radius (i.e., the bandwidth $w_i$) to construct a probability component for the given root that will be employed in generating a probability density function. Specifically, the template probability is centered on the center frequency $f_i$, and the width of the template probability is set at the bandwidth $w_i$. This is given by the following formula:

$$P(f) = \Sigma T((f-f_i)/w_i) w_i$$

where P is the probability function, f is the frequency, and T is the template function. An example is provided in FIG. 8 in which four exemplary roots of the numerator polynomial are applied to a triangular template probability to form four probability components (indicated at the numerals 24, 28, 32, and 36) which are combined to form an exemplary probability function as indicated at the numeral 40. Typically, P is normalized such that the integral of P over f equals 1, i e., making P into a probability density function. An example of an actual probability density function is depicted generally in FIG. 9 which depicts a peak at approximately 150 Hz, and which is a very narrow peak that is indicative of a high likelihood of snoring phenomenon at this frequency.

While a triangular template function is employed herein for purposes of providing an example, it is understood that other types of template probabilities can be employed. Other template probabilities that are likely usable would include rectangular template probabilities, Gaussian template probabilities, and other such template probabilities without limitation. It is further noted that the units are fixed and that height typically is proportional to 1/w, by way of example.

Additionally, it may be advantageous to consider whether those clusters whose phase is "unknown" might be relabeled as "inhale" or "exhale", by way of example, based upon consistency between the spectral characterizations of those unknown segments with the spectral characterizations of the inhale and exhale clusters. This can be referred to as a pooling of the clusters.

At stage three, the spectral characterization of each time instant or time segments in the signal is compared to the characterization of the clusters (or of the segments that are assigned to those clusters) that have been output at stage two. This enables a class assignment or at least a probability to be output for each time instant or time segment.

Additionally, the integrity of the temporal structure can be checked by confronting the class assignment (or the probabilities) with the temporal logic of breathing, i.e., inhale phase followed by exhale phase followed by rest phase, with a certain cadence which is a part of the data which is qualitatively known, i.e., such as having been measured at stage one, if possible. At this stage, one can use non-identified (i.e., non-cluster assigned) segments inasmuch as certain parts of the measurement data may not necessarily lend itself to the analysis set forth above. This may be, for instance, as a result of dominant background noises, or due to other phenomena.

Additionally, the clusters may be compared with or augmented with clusters that may be available in a database or that may be otherwise available. An example would be in which the clusters of a sleep period on a given day might be compared with the clusters that were generated during a sleep period the previous night or on another occasion. The output of stage three is a fully categorized time axis wherein all of the instances of time or the segments of time are fully categorized as being an inhalation phase, an exhalation phase, or a rest phase of a breathing cycle. FIG. 7 depicts an exemplary limited portion of such a categorized time axis.

With respect to stage four, it is understood that by having clusters described by their spectral characterization, and by having the various times at which such segments in such clusters begin and end, various overviews and analyses can be created and generated to give insight into the measurements that are exemplified by the categorized time axis. In its simplest form, stage four would be to render the information of the various clusters in one form or another and to provide an output. The output may be a series of plots showing, per cluster, statistics of the spectral behavior (i.e., mean and standard deviation per frequency, or median and quartile range), the total duration of the night, the relative duration of the night where relative can be relative to the total time or specific phase of the respiration time, and/or percentage of the respiration cycles in which such behavior is observed.

Alternatively, the data may be interpreted by using a knowledge engine or database in order to give meaning or interpretation to the events, and the output of the system may be a characterization in terms of a comparison to certain labels in the knowledge base or in the database. For instance, it is understood that certain snoring can arise or can change its character depending upon the consumption of alcohol before sleeping. Likewise, the characterization of snoring can change with excess age, with nasal obstruction, etc.

Such labels may be included in an output. Still alternatively, the data may be compared with data collected on previous days in order to generate a trend analysis and to output the results of such a trend analysis. Other types of other outputs will be apparent.

It thus can be seen that the aforementioned methodologies advantageously enable the characterization of a patient's disordered breathing during a sleeping period. Such an analysis is made possible, at least in part, by the WLP and LLP analysis methods that are mentioned herein. This is particularly so inasmuch as the vector B with its $b_k$ parameters characterized the filters and requires very little data elements to do so. For instance, in a tenth order system such as is described herein where K=10, a transfer function H (z) can effectively be characterized by the ten b parameters. In the absence of WLP or LLP, conventional sampling of a data signal would produce an enormous number of data that would be impractical to process over the course of an entire sleeping period. For instance, the use of conventional audio sampling at 30 kHz would result in 1.8 million data values per minute of sleep. Inasmuch as humans typically sleep six to eight hours per day, the generation of 1.8 million data values per minute of sleep would generate an amount of data that would be incapable of being meaningfully processed using conventional data processing equipment. On the other hand, if a filter function can be characterized in terms of ten b values, the data processing that is required is many orders of magnitude less than what would otherwise be needed in the event of strict sampling of signals and the storage of such samples. As such, the use of WLP and LLP advantageously enables data processing to occur using conventional data processing equipment where it otherwise would be impractical or impossible. Advantageously, therefore, the analyses presented herein are capable of being performed on contemporary computer equipment whereas in the absence of WLP and LLP this would not be possible. Other advantages will be apparent.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of characterizing a patient's disordered breathing during a sleeping period, comprising:
    receiving at least a first signal that is representative of the sounds occurring during at least a portion of the sleeping period in the vicinity of the patient;
    identifying in the at least first signal a plurality of segments by:
        subjecting at least a portion of the at least first signal to a linear prediction algorithm to obtain an excitation signal that is representative of the at least portion of the at least first signal,
        identifying as a plurality of candidate transition points in the excitation signal a plurality of simultaneous occurrences of a low energy level and a change in the excitation signal between a slope and another slope,
        determining that a plurality of portions of the excitation signal that exist between pairs of candidate transition points are similar to one another based at least in part upon similarity of the period and the spectral content of the plurality of portions, and
        based at least in part upon the determining, concluding that
            the pairs of candidate transition points are actual transition points,
            a portion of the excitation signal that immediately precedes each actual transition point is an inhalation phase of a breathing cycle, and
            a portion of the excitation signal that immediately follows each actual transition point is an exhalation phase of a breathing cycle; and
    generating an output that comprises at least an overview of a frequency spectrum during at least one of the inhalation phases and the exhalation phases.

2. The method of claim 1, wherein the linear prediction algorithm employs a tapped-delay line filter.

3. The method of claim 1, wherein the linear prediction algorithm employs a filter structure comprising at least one parameter tunable for providing enhanced detail in at least one specific part of the frequency spectrum.

4. The method of claim 3, wherein the linear prediction algorithm is a Laguerre linear prediction algorithm.

5. The method of claim 3, wherein the linear prediction algorithm is a warped linear prediction algorithm.

6. The method of claim 1, wherein the identifying as the plurality of candidate transition points in the excitation signal a plurality of simultaneous occurrences of a low energy level and a change in the excitation signal between a slope and another slope comprises using short-term polynomial decomposition.

7. The method of claim 1, wherein the determining that the plurality of portions of the excitation signal that exist between pairs of candidate transition points are similar to one another comprises applying an autocorrelation function.

8. The method of claim 1, wherein the identifying as the plurality of candidate transition points in the excitation signal a plurality of simultaneous occurrences of a low energy level and a change in the excitation signal between a slope and another slope is performed by a trained classifier.

9. The method of claim 1, wherein the low energy level refers to an envelope.

* * * * *